United States Patent [19]
Bushman

[11] Patent Number: 5,452,089
[45] Date of Patent: * Sep. 19, 1995

[54] OBJECT LOCATOR

[75] Inventor: Boyd B. Bushman, Lewisville, Tex.

[73] Assignee: Lockheed Corporation, Fort Worth, Tex.

[*] Notice: The portion of the term of this patent subsequent to Nov. 23, 2010 has been disclaimed.

[21] Appl. No.: 94,275

[22] Filed: Jul. 5, 1993

Related U.S. Application Data

[63] Continuation-in-part of Ser. No. 851,281, Feb. 7, 1992, Pat. No. 5,264,916, and Ser. No. 947,281, Sep. 17, 1992, Pat. No. 5,345,308.

[51] Int. Cl.$^6$ .............................................. G01J 04/00
[52] U.S. Cl. .................................. 356/364; 359/371; 359/407; 359/501; 250/330; 250/342
[58] Field of Search ............... 356/364, 366, 367, 368; 359/371, 386, 407, 483, 485, 501; 250/330, 342

[56] References Cited

U.S. PATENT DOCUMENTS

| | | |
|---|---|---|
| 2,165,974 | 7/1939 | Land . |
| 3,192,825 | 7/1965 | Courtney-Pratt et al. . |
| 3,633,212 | 1/1972 | Cooper . |
| 4,202,601 | 5/1980 | Burbo et al. ........................ 350/157 |
| 4,515,443 | 5/1985 | Bly . |
| 4,601,552 | 7/1986 | Jessmore ............................ 350/551 |
| 4,763,361 | 8/1988 | Honeycutt et al. . |
| 5,138,162 | 8/1992 | Hacskaylo . |
| 5,264,916 | 11/1993 | Bushman ............................ 356/364 |

OTHER PUBLICATIONS

"Polarization Optics Catalog & Handbook", 1992 (p. 10–15).
"NASA Tech Briefs", May, 1993 vol. 17 No. 5 (p. 52).
"Technical Support Package, Device for Perception of Polarization", MSC-21915.
AI S. N. 07/863,883, filed Apr. 6, 1992, Victor S. Whitehead and Kinsel Coulson.

Primary Examiner—Mark Hellner
Attorney, Agent, or Firm—James E. Bradley

[57] ABSTRACT

A search light employs variable polarization angles to enhance target identification. The search light shines a beam of light which may be directed across terrain. The beam of light is alternated in polarization angles at a rate of about five to twelve cycles per second. The alternating contrast in polarization angles produces flashing to an observer viewing certain targets struck by the beam of light. The flashing appears when striking man-made objects which tend to have a differential in polarized light between horizontal and vertical polarization. Natural objects do not appear to provide the flashing to the observer. The rotating polarization angles are accomplished in one instance by using a stationary polarizer and a liquid crystal retarder mounted in front of a light source. In another instance, the change in polarization angles is accomplished by rotating a polarizer in front of a light source. The light source may be infrared, visible or ultraviolet.

30 Claims, 2 Drawing Sheets

OBJECT LOCATOR

CROSS REFERENCE TO RELATED APPLICATION

This application is a continuation in part of Serial No. 07/851,281, filed Feb. 7, 1992, now U.S. Pat. No. 5,264,916, Object Detection System, and of Serial No. 07/947,281, filed Sep. 17, 1992, now U.S. Pat. No. 5,345,308 Object Discriminator, both invented by Boyd B. Bushman. Also, a patent application is being simultaneously filed by the same inventor entitled Object Locator, which contains some common subject matter with this application.

BACKGROUND OF INVENTION

1. Field of the Invention

This invention relates in general to detecting objects by detecting light reflections from an object, and in particular, to a system that utilizes a search light which employs a polarizer that alternates polarization angles of the beam of light emanating from the search light.

2. Description of Prior Art

This invention deals with a method of detecting objects, such as military targets. The targets may be trucks, tanks, artillery, aircraft, command centers and other systems. These objects may be protected by camouflage, foliage, or may be painted with a camouflage paint.

Presently, objects are detected visually through binoculars. Objects may also be detected by other techniques such as radar, infrared and night vision amplification systems. The prior systems do not always adequately detect an object, particularly objects that are camouflaged.

There are needs for detecting objects other than in military applications also. For example, the highest reason for helicopter crashes is due to collisions with high-tension electric wires, guide wires or other suspended cables. These cables are difficult to see by the pilot. At present, there is no particular means for detecting such cables other than visually.

SUMMARY OF INVENTION

In this invention, a search light unit is employed for detecting objects. The search light has a light source that may be visible light, or it may be near infrared, infrared, or ultraviolet. The light source is focused into a beam of light that will sweep a terrain. The search light also employs a polarizer. The polarizer is of a conventional type having a large number of very finely spaced parallel lines to linearly polarize light at one angle.

In one embodiment, a liquid crystal retarder mounts in front of the polarizer, receiving light from the light source after it has been polarized by the polarizer. The liquid crystal retarder rotates light rays 90 degrees. An electronic circuit will alternately shift the liquid crystal retarder between the rotated and non-rotated mode. The beam from the light source thus passes through the polarizer and the liquid crystal retarder, which when actuated, will alternately shift the light rays 90 degrees, then back. This procedure alternately changes the angle of polarization of the light beam.

It has been found that when the light beam impinges on man-made objects, such as military vehicles, flashing appears and can be observed by an observer who is spaced away from the beam of light. Preferably, the observer uses a lens array, and the flashing is enhanced if the observer also views through a stationary polarizer. The rate of flashing is in proportion to the speed of the cycles of the liquid crystal retarder. Background objects, such as trees, rocks and the like do not appear to have the flashing due to alternating polarization angles.

In another embodiment, the polarization angle is alternately shifted 90 degrees by rotating a conventional polarizer. The polarizer is mounted for rotation in the housing. A motor engages the polarizer to cause it to rotate. As it rotates, it will alternate the polarization angles between horizontal and vertical polarization.

The observer may employ a conventional optical scope mounted to a weapon. The observer may also utilize a polarizer filter mounted to the optical scope to enhance the flashing that occurs when the search light beam strikes man-made objects. Furthermore, the scope may be of an infrared or a night vision amplification type.

In another embodiment, the observer employs a video camera. The video camera will scan and detect the flashing caused by the search light beam. The video camera may also use an electronic notch filter which assists in removing backgrounds which do not reflect a flashing light due to the change in polarization angle. The notch filter filters a range of frequencies below a selected cut-on level. The notch filter passes a lower level of frequencies necessary for the video camera operations, such as sweep.

DETAILED DESCRIPTION OF INVENTION

Figure 1:
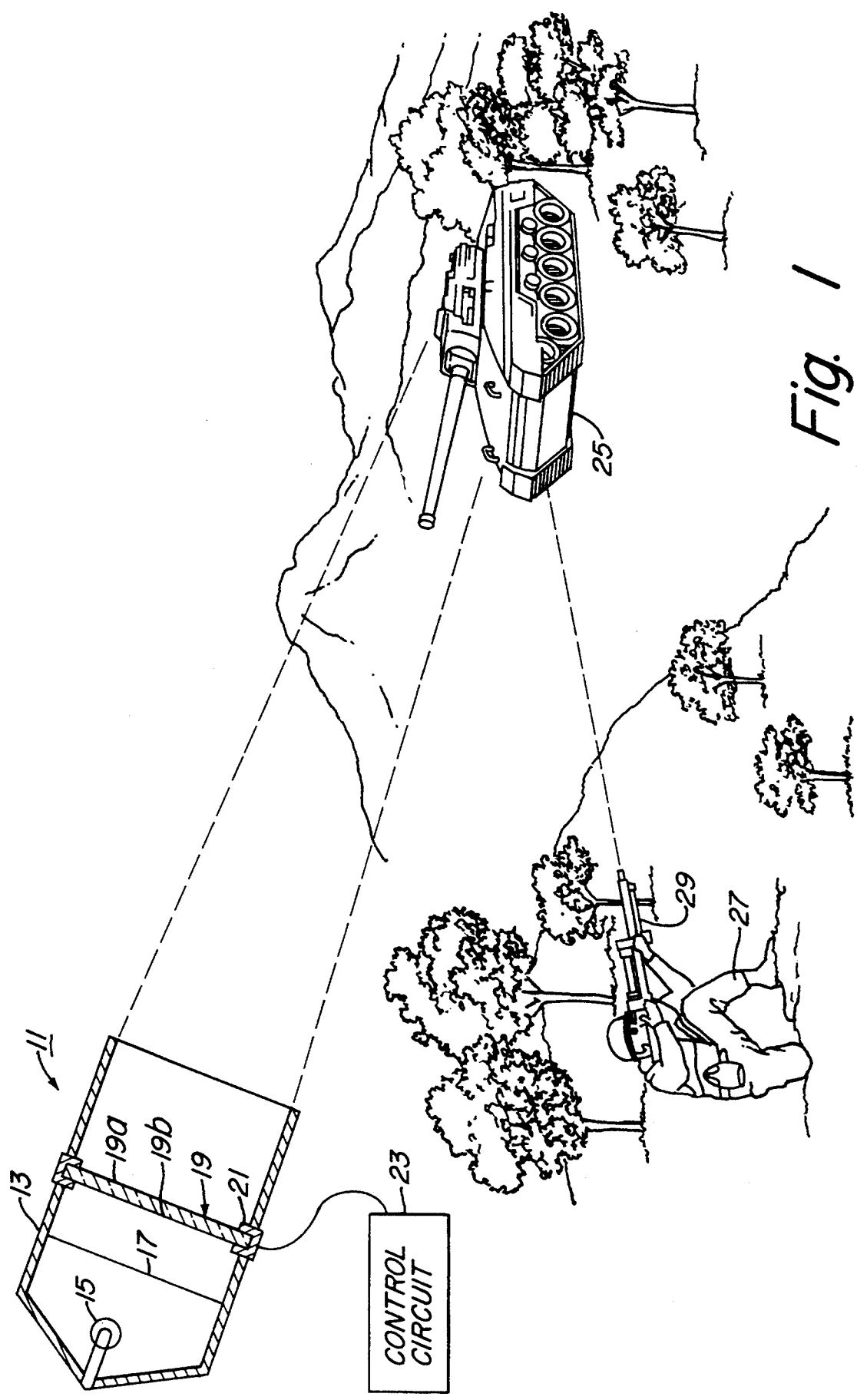
FIG. 1 shows a search light unit constructed in accordance with this invention, and also showing an observer and a target, the search light unit being shown in section and schematically illustrated.

Referring to FIG. 1, the search light 11 has a housing 13. A light source 15 will be mounted to the rear of housing 13 for shining a beam of light. The type of light source may be visible light, near infrared or infrared for night use, or ultraviolet in some instances. Near infrared and infrared will both be referred to herein as "infrared" for simplicity. The power of the light source 15 and the lens system employed will depend upon the range desired.

A polarizer 17 mounts stationarily in housing 13 directly forward of light source 15. Polarizer 17 is of a conventional type. Polarizer 17 has a large number of lines formed thereon, which may be scribed or otherwise etched on the surface. Also, polarizer 17 may be formed by a chemical coating which aligns the molecules in parallel lines. The lines are extremely closely spaced and are parallel to each other. The distance between the lines will be less than the wavelength of the light for which the polarizer is designed. Polarizers are available for visible light as well as infrared and ultraviolet light.

Polarizer 17 is stationarily mounted to housing 13. The lines may be oriented horizontally, vertically, or at another angle. If oriented horizontally, horizontal components of the light rays emanating from light source 15 will be unable to pass through the finely divided lines. Vertical and other components will pass through.

In the embodiment in FIG. 1, a liquid crystal retarder 19 mounts directly in front of polarizer 17. Liquid crystal retarder 19 has a forward plate 19a and a rearward plate 19b with a liquid crystal substance sandwiched there between. The thickness of retarder 19 is greatly exaggerated in FIG. 1. The plates 19a and 19b are mounted in a metal ring 21, which is stationarily mounted to housing 13.

A control circuit 23 will supply an alternating voltage to retarder 19. At one voltage, which may be zero, retarder 19 will be in a non-rotated mode, which allows light passing through polarizer 17 to pass undeflected through retarder 19. Retarder 19 is substantially transparent in this mode, passing approximately 97% of the light. At the other voltage level, retarder 19 will deflect or rotate the polarized light 90 degrees. This 90 degree shift changes the angle of polarization. The control circuit 23 has a frequency control which will vary the rate of oscillation between the rotated and non-rotated modes. Preferably, the rate is fairly slow, sufficient so that an observer can detect flashing that results as shall be explained subsequently. The rate is preferably approximately five to twelve cycles per second.

Retarders 19 of this type, including circuit 23, are commercially available. One manufacturer is Meadowlark Optics, 7460 Weld County Road 1, Longmont, Colo. 80504. A variable liquid crystal retarder that has demonstrated utility for this invention is manufactured by such company under the model number B1020. The same company also manufactures the control circuit 23 which is a part of retarder 19.

Figure 3:
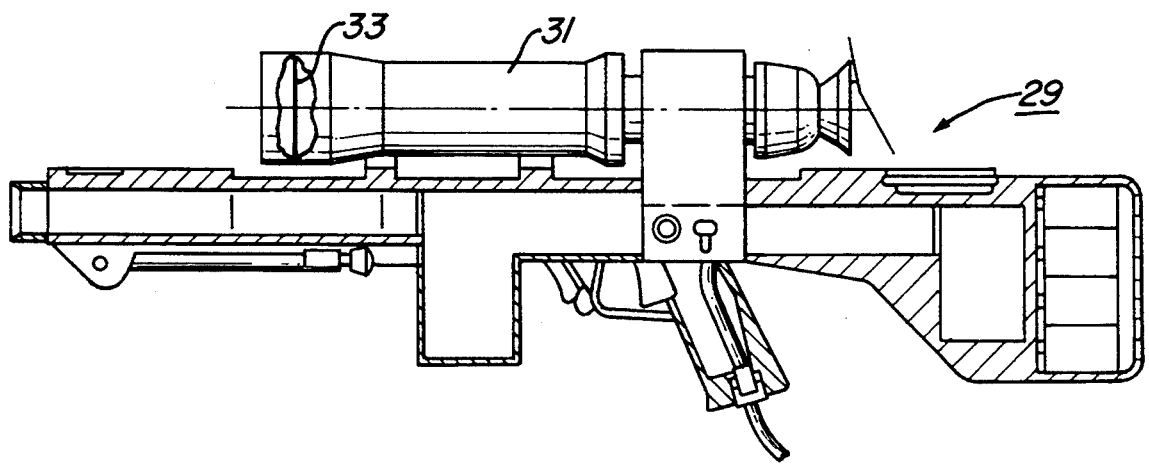
FIG. 3 is a side view, partially sectioned, illustrating a weapon having a scope for observing objects highlighted by the search light unit of FIGS. 1 or 2.

The beam of light will be used to scan a territory in which enemy objects may be expected. The beam of light is shown impinging on a tank 25. The perspective in FIG. 1 is greatly distorted, as tank 25 would be much farther away. A soldier 27 is shown remotely located from search light 11. Solder 27 is carrying a weapon 29 which may be used to fire on tank 25. As shown in FIG. 3, weapon 29 may be conventional. Observing may be enhanced by a scope 31, which has an optical lens array. The lens array may be of a visible light type, or it may be of a night amplification type, or a type which detects infrared radiation. Preferably a polarizer 33 is stationarily mounted in the lens array of scope 31. Polarizer 33 may be oriented with its lines horizontal, vertical or other angles.

It has been found that certain objects illuminated by the beam of light from search light 11 will appear to flash in proportion to the cycling of the liquid crystal retarder 19 between the rotated and non-rotated modes. Light reflected from many man-made objects will appear to flash to soldier 27. The flashing is enhanced by the use of polarizer 33 (FIG. 3). Most natural objects in the background will not flash, because the reflected light from natural surfaces usually does not produce a strong polarizing contrast. The flashing will assist in pinpointing military targets to soldier 27.

The flashing is readily discernable regardless of the orientation of the lines of the polarizers 17, 33. For example, if polarizer 17 and polarizer 33 are oriented with their lines horizontal, then vertical surfaces of tank 25 may appear bright when retarder 19 is in the non-rotated mode. Horizontal portions of the object may appear dull because the light reflected therefrom will be polarized by the polarizer 33. The light reflected from the vertical surfaces of the object will not be polarized by the polarizer 33 when the lines of polarizer 33 are oriented horizontally. When retarder 19 is alternated to the rotated mode, however, there is a change. Now, vertical surfaces will appear less bright, and horizontal surfaces will appear brighter. Even without polarizer 33, the flashing can be observed, but the flashing is enhanced by the use of polarizer 33.

If the light source 15 is infrared, the beam of light will not be visible to the enemy or the occupants of tank 25. The scope 31 will detect the flashing due to the change in polarization angle even if tank 25 is not moving and has cooled down to that of its ambient surroundings. Conventionally, an infrared detector will detect a stationary object only if it has a temperature different than its surroundings. Consequently, a tank that has not been operated recently would not be observable under prior art techniques. With this system, however, the flashing will appear to the observer 27, who will be employing an infrared detector, because the flashing does not appear from background objects such as hills, trees and the like, whether with the light source 15 is infrared or visible. Similarly, ultraviolet light is not visible to the enemy, yet flashing due to changing polarization angles can be detected by an ultraviolet detector.

Figure 2:
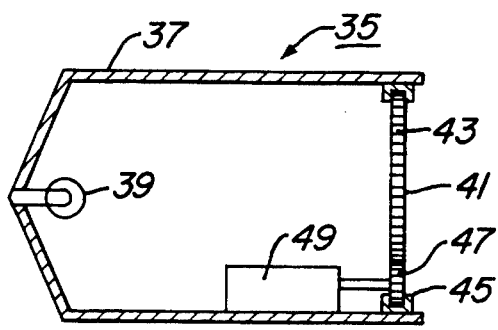
FIG. 2 is a sectional schematic illustration of an alternate embodiment of the search light unit in FIG. 1.

FIG. 2 shows an alternate embodiment for search light 11. In this embodiment, search light 35 also has a housing 37 and a light source 39 which creates a light beam. Light source 39 may be emanating visible light, infrared or ultraviolet. Polarizer 41, however, is not stationarily mounted in housing 37 as is polarizer 17 of FIG. 1. Rather, polarizer 41 is mounted for rotation about a longitudinal axis of housing 37. Polarizer 41 is of a conventional type, having finely divided lines. A drive means will allow polarizer 41 to rotate at variable speeds. The drive means in this instance comprises gear teeth 43 upon the perimeter of polarizer 41. Bearings 45 support polarizer 41 for rotation in housing 37. A pinion gear 47 engages gear teeth 43 to rotate polarizer 41. An electric motor 49 will control the speed of rotation of pinion gear 47.

In the embodiment of FIG. 2, a liquid crystal retarder, such retarder 19 of FIG. 1, is not required. Rather, the polarization angle is rotated physically by rotating polarizer 41. The flashing to observer 27 appears just as in the instance of FIG. 1. The speed of rotation may be the same as employed with the rate of oscillation of retarder 19 of FIG. 1. The detecting unit 31 employed by observer 27 will be the same as in FIG. 1.

Figure 4:
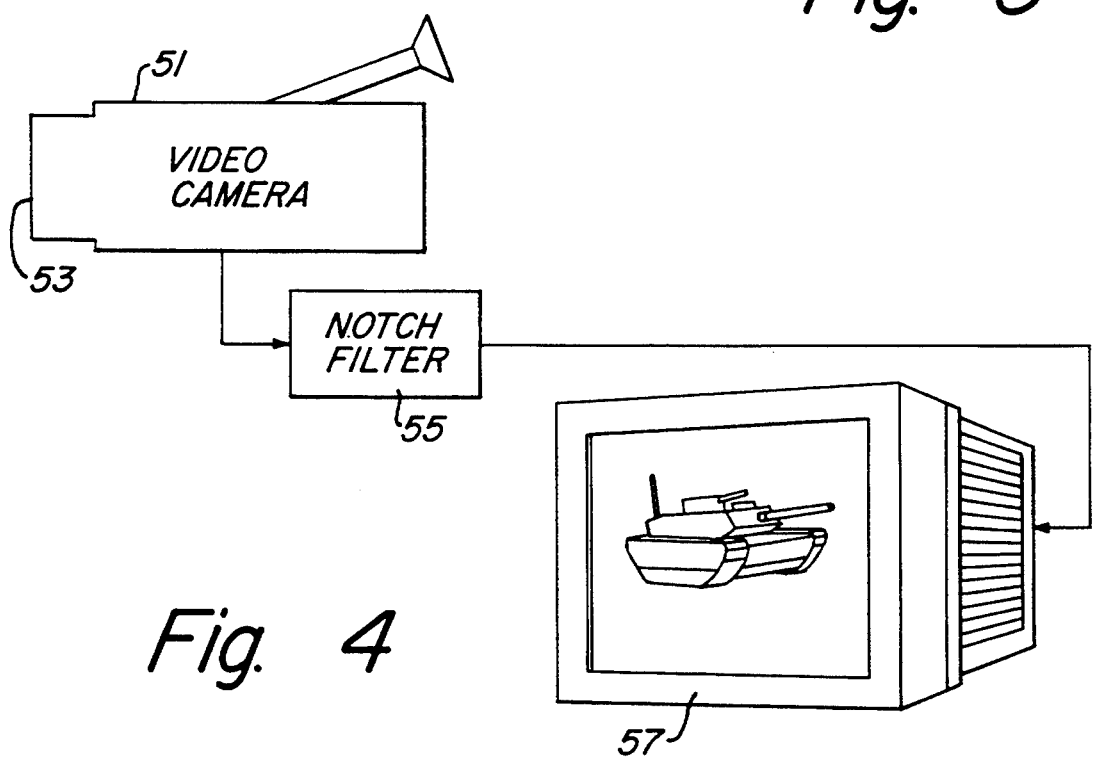
FIG. 4 illustrates a video camera used to observe objects being highlighted by the search light unit of FIGS. 1 or 2.

FIG. 4 illustrates an alternate embodiment of a observing or detection unit. In this embodiment, a video camera 51 is employed for observing objects such as tank 25 which have been struck with a beam of light from either search light 11 or search light 35. Video camera 51 is a conventional video camera. Objects viewed by video camera 51 are converted into electrical signals which are displayed electronically. Preferably a polarizer 53 will be mounted stationarily to the video camera 51 at the front of the image path. A conventional signal processor in video camera 51 will produce analog electrical signals proportional to the objects viewed. In a conventional camera system, these signals may be recorded on video tape or film. Also, the signals may pass to a conventional television monitor 57 for viewing.

Preferably, the electrical signals from video camera 51 first pass through a notch electronic filter 55 before being displayed on monitor 57. Notch filter 55 is of a type which will pass signals above a high level cut-on frequency, preferably 100 KHZ and block, filter, or delete those in a range below, all of which processes are referred to herein as "filtering". The notch filter 55 also passes frequencies below 17,750 HZ, as those frequencies are needed for operation of the video camera monitor 57 operations, such as sweep, that are not directly related to the scene being viewed. This high cut-on or selected frequency is selected to be high enough to eliminate much of the background objects which reflect light that is not affected by the beam of light from the search lights 11 or 13. That is, these objects will not appear to have any flashing to an observer when struck by the beams of light from the units 11 or 35 as the polarization angles oscillate. The high cut-on or selected frequency of filter 55 is much higher than the frequency of rotation of polarizer 41, or the rate of cycling of retarder 19. Filter 55 is preferably variable so that its high cut-on or pass frequency can be varied.

The user will watch monitor 57 while an object has been illuminated by a beam of light from the search lights 11 or 35. Light reflected from man-made objects will appear to flash due to the rate of rotation of polarizer 41, or the rate of oscillation of retarder 19. Most natural objects in the background will not flash, because the reflected light from natural surfaces usually does not produce a strong polarization contrast. The user adjusts filter 55 until much of the background is eliminated, but the flashing man-made objects due to the beam of light from the search lights 11 or 35 remain visible.

In one embodiment, employing a conventional video camera and an adjustable filter 55, the high cut-on frequency was determined to be effective if set in the range of 100 KHZ (Kilohertz), to 2 MHZ (Megahertz). While in this range, flashing objects due to the search lights 11 or 35 were enhanced and background objects, such as sky, foliage and concrete were reduced and roughened.

The invention has significant advantages. The flashing due to the change in polarization enables an observer to pinpoint targets. The observer may be close to the search light, if the search light is mounted on a vehicle. The observer may also be remotely located. The search lights can be used in poor light conditions, such as at night. The search lights can also be employed with infrared at night. An enemy would not be aware of the searching and detection process occurring because the infrared light would not be visible to the enemy. The system allows man-made objects to be detected even if they have cooled down to temperatures of ambient conditions.

While the invention has been shown in only a few of its forms, it should be apparent to those skilled in the art that it is not so limited but is susceptible to various changes without departing from the scope of the invention.

I claim:

1. A method for searching for selected objects, comprising:
    passing a beam of light through a polarizer into a view field that may contain selected objects, the polarizer causing the beam of light to polarize at a polarizing angle;
    alternately changing polarizing angle as the beam of light passes through the polarizer; and
    viewing objects contacted by the beam of light from a viewpoint other than through the polarizer to determine if flashing exists due to the alternating changing polarizing angle as the beam of light contacts certain objects.

2. The method according to claim 1 wherein the step of viewing the objects comprises viewing the objects through another polarizer.

3. The method according to claim 1 wherein the step of viewing the objects comprises:
    providing a lens array which will define an image path; and
    mounting another polarizer stationarily to the lens array and viewing the objects through said another polarizer.

4. The method according to claim 1 wherein:
    the step of passing a beam of light through the polarizer comprises passing infrared light through the polarizer; and
    the step of viewing the objects comprises viewing the objects with an infrared detector.

5. The method according to claim 1 wherein:
    the step of passing a beam of light through the polarizer comprises passing visible light through the polarizer; and
    the step of viewing the objects comprises viewing the objects with an optical lens array which provides an image path for visible light for objects being viewed.

6. The method according to claim 1 wherein:
    the step of passing a beam of light through the polarizer comprises passing visible light through the polarizer; and
    the step of viewing the objects comprises viewing the objects with a video camera and providing electrical signals from the video camera in response to the objects viewed; and
    filtering the electrical signals produced by the video camera in a range below a frequency which is selected to substantially reduce the display of background objects viewed which reflect light that does not appear to flash due to the alternating changing polarizing angle, and passing the electrical signals produced by the video camera above the selected frequency.

7. The method according to claim 1 wherein the step of alternately changing the polarizing angle comprises:
    providing a liquid crystal retarder which has a nonrotated mode wherein the beam of light passes through the retarder substantially without effect, and when a voltage is applied, has a rotated mode which rotates the beam of light; and
    alternately applying said voltage to change the retarder from the nonrotated mode to the rotated mode and passing the beam of light through the polarizer.

8. The method according to claim 1 wherein the step of alternately changing the polarizing angle comprises:
    providing a liquid crystal retarder which has a nonrotated mode wherein the beam of light passes through the retarder substantially without effect, and when a voltage is applied, has a rotated mode which rotates the beam of light 90 degrees; and
    alternately applying said voltage to change the retarder from the nonrotated mode to the rotated mode and passing the beam of light first through the polarizer and then through the retarder.

9. The method according to claim 1 wherein the step of alternately changing the polarizing angle comprises: rotating the polarizer about an axis of the polarizer.

10. The method according to claim 1 wherein the step of alternately changing the polarizing angle is conducted at a rate selected such that the flashing is discernable to a human eye.

11. The method according to claim 1 wherein:
the beam of light is an infrared light;
the step of alternately changing the polarizing angle comprises:
providing a liquid crystal retarder which has a nonrotated mode wherein the beam of light passes through the retarder substantially without effect, and when a voltage is applied, has a rotated mode which rotates the beam of light;
alternately applying said voltage to change the retarder from the nonrotated mode to the rotated mode and passing the beam of light first through the polarizer and then through the retarder; and
the step of viewing the objects comprises viewing the objects with an infrared detector.

12. A method for searching for selected objects, comprising:
passing a beam of light through a first polarizer into a view field which may contain objects of interest, the first polarizer polarizing the beam of light at a first polarizing angle;
alternately changing the first polarizing angle to a second polarizing angle, 90 degrees from the first polarizing angle, as the beam of light passes through the first polarizer; and
viewing through a second polarizer and a lens array the objects contacted by the beam of light from a viewpoint other than through the first polarizer; and
determining if flashing of images of the objects viewed exists due to the alternating first and second polarizing angles of the beam of light as it contacts certain objects.

13. The method according to claim 12 wherein:
the step of passing a beam of light through the first polarizer comprises passing infrared light through the first polarizer; and
the step of viewing the objects comprises viewing the objects with an infrared detector.

14. The method according to claim 12 wherein the step of alternately changing the first polarizing angle to the second polarizing angle comprises:
providing a liquid crystal retarder which has a nonrotated mode wherein the beam of light passes through the retarder substantially without effect, and when a voltage is applied, has a rotated mode which rotates the beam of light 90 degrees; and
alternately applying said voltage to change the retarder from the nonrotated mode to the rotated mode after the beam of light has passed through the first polarizer.

15. The method according to claim 12 wherein the step of alternately changing the first polarizing angle to a second polarizing angle comprises:
rotating the first polarizer about an axis of the first polarizer.

16. A method for searching for selected objects, comprising:
providing a beam of light;
passing the beam of light through a stationarily mounted polarizer to polarize the beam of light;
providing a liquid crystal retarder which has a rotated mode and a nonrotated mode;
passing the polarized beam of light through the retarder;
alternately applying voltage to change the retarder from the nonrotated mode to the rotated mode, causing polarizing angles to alternately change, and directing the beam of light at a view field where there may be objects of interest;
viewing the objects contacted by the beam of light from a viewpoint other than through the polarizer; and
determining if flashing of images of the objects viewed exists due to the alternating polarizing angles.

17. The method according to claim 16 wherein:
the step of providing the beam of light comprises providing a beam of infrared light; and
the step of viewing the objects comprises viewing the objects with an infrared detector.

18. The method according to claim 16 wherein:
the step of providing a beam of light comprises providing a beam of visible light;
the step of viewing the objects comprises viewing the objects with a video camera and providing electrical signals from the video camera in response to the objects viewed; and
filtering the electrical signals produced by the video camera in a range below a selected frequency which is selected to substantially reduce the display of background objects viewed which reflect light that does not appear to flash due to the changing polarizing angles of the beam of light.

19. An apparatus for searching for selected objects, comprising:
means for passing a beam of light through a polarizer to polarize the beam of light at a polarizing angle;
means for alternately changing the polarizing angle of the beam of light as it passes through polarizer; and
means for viewing the objects contacted by the beam of light from a viewpoint other than through the polarizer to determine if flashing exists due to the alternating changing polarizing angle as the beam of light contacts certain objects.

20. The apparatus according to claim 19 wherein the means for viewing the objects includes another polarizer through which the objects are viewed.

21. The apparatus according to claim 19 wherein the means for viewing the objects comprises:
a lens array which will define an image path; and
another polarizer stationarily mounted to the lens array.

22. The apparatus according to claim 19 wherein the beam of light is infrared light; and
the means for viewing the objects comprises an infrared detector.

23. The apparatus according to claim 19 wherein the beam of light is visible light; and
the means for viewing the objects comprises an optical lens array which provides an image path for visible light for objects being viewed.

24. The apparatus according to claim 19 wherein the beam of light is visible light; and
the means for viewing the objects comprises:

a video camera which provides electrical signals in response to the objects viewed; and means for filtering the electrical signals produced by the video camera in a range below a selected frequency which is selected to substantially reduce the display of background objects viewed which reflect light that does not appear to flash due to the alternating changing polarizing angle, and for passing the electrical signals produced by the video camera above the selected frequency.

25. The apparatus according to claim 19 wherein the means for alternately changing the polarizing angle of the beam of light comprises:

a liquid crystal retarder which has a nonrotated mode wherein the beam of light passes through the retarder substantially without effect, and when a voltage is applied, has a rotated mode which rotates the beam of light.

26. The apparatus according to claim 19 wherein the means for alternately changing the polarizing angle of the beam of light comprises:

means for rotating the polarizer about an axis of the polarizer.

27. An apparatus for searching for selected objects, comprising:

source means for providing a beam of light for shining on a view area that might contain one of the selected objects;

a first polarizer through which the beam of light passes, causing the light to polarize at a first polarizing angle;

means for alternately changing the first polarizing angle to a second polarizing angle, 90 degrees from the first polarizing angle, as the beam of light passes through the first polarizer;

a second polarizer located out of the beam of light;

view means for viewing through the second polarizer the objects contacted by the beam of light from a viewpoint other than through the first polarizer to determine if flashing exists due to the alternating first and second polarizing angles.

28. The apparatus according to claim 27 wherein the beam of light is infrared light; and the view means comprises an infrared detector.

29. The apparatus according to claim 27 wherein the means for alternately changing from the first polarizing angle to the second polarizing angle comprises:

a liquid crystal retarder which has a nonrotated mode wherein the beam of light passes through the retarder substantially without effect, and when a voltage is applied, has a rotated mode which rotates the beam of light.

30. The apparatus according to claim 27 wherein the means for alternately changing from the first polarizing angle to the second polarizing angle comprises:

means for rotating the first polarizer about an axis of the first polarizer.

* * * * *